(12) United States Patent
Chvapil

(10) Patent No.: US 7,199,156 B2
(45) Date of Patent: Apr. 3, 2007

(54) COMPOSITION AND METHOD TO TREAT SOLID TUMORS

(76) Inventor: Milos Chvapil, 5655 Mina Vista, Tucson, AZ (US) 85718

( * ) Notice: Subject to any disclaimer, the term of this patent is extended or adjusted under 35 U.S.C. 154(b) by 608 days.

(21) Appl. No.: 10/683,520

(22) Filed: Oct. 10, 2003

(65) Prior Publication Data

US 2005/0080132 A1    Apr. 14, 2005

(51) Int. Cl.
*A61K 31/275* (2006.01)
*A61K 31/22* (2006.01)
*A61K 31/13* (2006.01)

(52) U.S. Cl. .................. 514/528; 514/550; 514/663
(58) Field of Classification Search .................. None
See application file for complete search history.

(56) References Cited

U.S. PATENT DOCUMENTS

| 4,254,122 A | 3/1981 | Brown |
| 4,444,787 A | 4/1984 | Moorhead |
| 4,485,088 A | 11/1984 | Chvapil |
| 4,762,705 A | 8/1988 | Rubin |
| 6,686,336 B2 | 2/2004 | Nagasawa |

OTHER PUBLICATIONS

Wondrak et al., "Antimelanoma Activity of Apoptogenic Carbonyl Scavengers", The Journal of Pharmacology and Experimental Therapeutics, 2006, pp. 805-814, vol. 316, No. 2, The American Society for Pharmacology and Experimental Therapeutics, USA.
Miller, et al., Proc. Nat'l. Acad. Sci. 90,3304, 1993, pp. 3304-3308.

*Primary Examiner*—Johann Richter
*Assistant Examiner*—Nathan W Schlientz
(74) *Attorney, Agent, or Firm*—Dale F. Regelman; Chandler & Udall, LLP

(57) ABSTRACT

A method to treat an animal, including a human, having a solid tumor. The method provides a lipophilic lathyrogen. The method administers a therapeutically effective amount of the lipophilic lathyrogen within the solid tumor.

9 Claims, 3 Drawing Sheets

COMPOSITION AND METHOD TO TREAT SOLID TUMORS

FIELD OF THE INVENTION

Applicant's invention relates to a composition and method to inhibiting the growth of solid tumors using a one-time local injection of a lipophilic lathyrogenic derivative. In certain embodiments, Applicant's composition and method inhibits tumor growth by interfering with collagen crosslinking in the tumor stroma and microvessels.

BACKGROUND OF THE INVENTION

The cause of many diseases consists in abnormal accumulation and further crosslinking of collagen structures in the tissue. It is known in the art that crosslinking of collagen at the site of an injury, whether caused by trauma or surgical intervention, often results in scar contractures, strictures or stenosis of tubular organs, including for example the urethra, esophagus, trachea, and the like. Other effects include fibrotic adhesion to the tendon or nerve after trauma or surgical intervention, or stiffness of the joints after longer immobilization. Studies using laboratory animals, and human trials, indicate that daily administration of certain hydrophilic lathyrogens for a longer time period, reduces the disease symptoms related to collagen deposition or crosslinking.

Lathyrogens D-Pencillamine ("DPA") and beta-aminopropionitrile ("BAPN") block the function of the enzyme, lysyl oxidase (L.O), which initiates the formation of the first step in the process of collagen crosslinking.

DPA

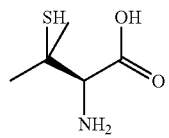

BAPN

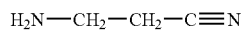

Non-crosslinked collagen does not form fibrils and lacks sufficient mechanical strength to produce strictures (urethral, stenosis esophagus, trachea) or contractures (after third degree burns).

Table I summarizes certain known properties of BAPN and DPA.

TABLE I

| Characteristic | BAPN-F | D-PA |
|---|---|---|
| Classification | lathyrogen | Lathyrogen + chelating agent |
| Effect on collagen | specific block lysyl oxidase, irreversibly | chelates copper of L.O. Binds to aldehydes, prevents formation of crosslinks Cleaves nonreduced Schiff base crosslinks |
| Clinical use | none | Rheumatoid Arthritis, Wilson disease, cystinuria |
| | IND-scleroderma peritendinous adhesions urethral strictures | intoxication by metals(Pb, Hg |
| Toxicity in systemic administration | yes | yes |
| In local administration | none | none |
| Interactions with other Metabolites | very specific for lysyl oxidase. Irreversible inhibitor. | metals (Cu, Fe, Zn), B6, |

It is known in the art that non-crosslinked collagen, i.e. not polymerized into collagen fibers, does not provide supporting stroma for cells and pericapillary sheath, i.e. basal lamina, in newly formed vessels. Furthermore, disintegrated collagen structure is more susceptible to degradation by the system of collagenases. As a result, treating a tumor with DPA inhibits tumor growth, and the treated structure regresses.

The clinically beneficial effects of orally administered DPA and/or BAPN are, however, marred by side toxic effects. These toxic side effects often force the discontinuation of the treatment. Nevertheless, DPA has been used clinically in systemic administration for more than forty (40) years in the treatment of Wilson disease (Cu accumulation), cystinuria, rheumatoid arthritis, scleroderma, metal poisoning and others, in spite of common occurrence of side toxic effects.

In order to mitigate the toxicity of DPA and/or BAPN, U.S. Pat. No. 4,485,088, in the name of Chvapil, teaches a method to treat fibrotic lesions by topical administration of lathyrogenic drugs, including DPA and BAPN. The '088 patent teaches a method wherein these drugs are administered locally or topically into or onto the site of the lesion. Using this treatment protocol, the dose was 100 to 200 times lower than that needed for similar effect when systemically administered. Topical administration of such lower dosages of DPA and/or BAPN did not produce local or systemic toxic effects.

Two major problems arose, however, with local administration of either lathyrogen. Firstly, these drugs need to be administered daily because they are quickly metabolized in tissues. Secondly, the strategic enzyme to be inhibited, i.e. lysyl oxidase (L.O.), is known to be rapidly resynthesized. Therefore, in order to achieve continuous inhibition of tumor growth, a stable concentration of the lathyrogen in the tissue is required. It is known in the art that after an injury the increased L.O. activity persists for 3–12 weeks, depending on the tissue affected. Therefore, daily continuous administration of the lathyrogen is required over 3 to 12 weeks post injury, depending on the type of the injury.

Applicant has discovered, however, that local intratumoral (ITI) injection of various therapeutic modalities produces the maximal concentration of the treatment within the target tissue with minimal outflow into the systemic circulation. See, Example IV, below. Therefore, repetitive local injections of one or more lathyrogens into a tumor minimize or completely avoid the occurrence of toxic side effects typical for most of chemotherapeutics or immunosuppressive drugs when administered systemically.

Several treatment options for local delivery of one or more lathyrogens exist. The simplest and most direct is injection into the tumor using a fine needle under the assistance of diagnostic imaging. Intra arterial injection is limited to those tumors comprising a recognizable artery, and is reported to result in lower delivery of the medication. Use of an implantable osmotic micropump requires surgical intervention.

Using Applicant's local injection into a tumor, the therapeutics can be delivered in a solvent, or in a polymeric delivery system. In either case, the structural characteristics of the therapeutics are important for obtaining the sustained release for a reasonable time period. These structural characteristics include molecular weight, electrical charge, and most importantly, the affinity to aqueous environment, i.e. hydrophilicity vs lipophilicity.

The use of DPA and/or BAPN, or salts VI and/or VII of these lathyrogenic compounds, for intra-tumoral injections ("ITI") is not feasible because of high water solubility. BAPN-F comprises Compound VII wherein $X^-$ is fumarate.

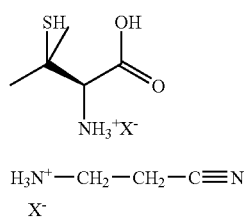

VI $H_3N^+-CH_2-CH_2-C\equiv N$
$X^-$

VII

Furthermore, disposing one or more of DPA, BAPN, Compound VI, and/or Compound VII in a polymeric carrier does not afford long-term release. Rather, these compounds are quickly washed out from the tissue within few hours. Therefore, Applicant chemically modified D-penicillamine or b-aminopropionitrile, the two most studied and effective representative of lathyrogenic substances, to form lipophilic derivatives. It was essential that such derivatization not block the functional groups responsible for the immediate lathyrogenic effects seen with DPA and/or BAPN.

With the exception of the '088 patent to Chvapil, use of local-topical administration of lathyrogenic substances for medical treatments is not known in the art. What is needed is a method for sustained administration of one or more lathyrogens, where those lathyrogens are released over a period of weeks following a single injection into the tissue. Both BAPN-F and DPA comprise small molecules, having molecular weights of 130 and 300 Daltons, respectively. Both compounds are also very soluble in aqueous media, such as tissue fluid. These molecular weight and solubility characteristics promote rapid diffusion of these drugs from the injection site, or fast release from a polymeric carrier. What is needed is a method to derivatize these lathyrogens to increase molecular weight and/or to reduce water solubility.

SUMMARY OF THE INVENTION

Applicant's invention includes a composition, where that composition includes a lipophilic lathyrogen dispersed within a polymeric carrier. Applicant's invention further includes a method to treat a solid tumor. In certain embodiments, Applicant's method injects Applicant's lipophilic lathyrogen into the tumor. In certain embodiments, Applicant's method disperses Applicant's lipophilic lathyrogen in a polymeric carrier, and then disposes the lipophilic lathyrogen/polymeric carrier composition in the solid tumor.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE PREFERRED EMBODIMENTS

Figure 1:
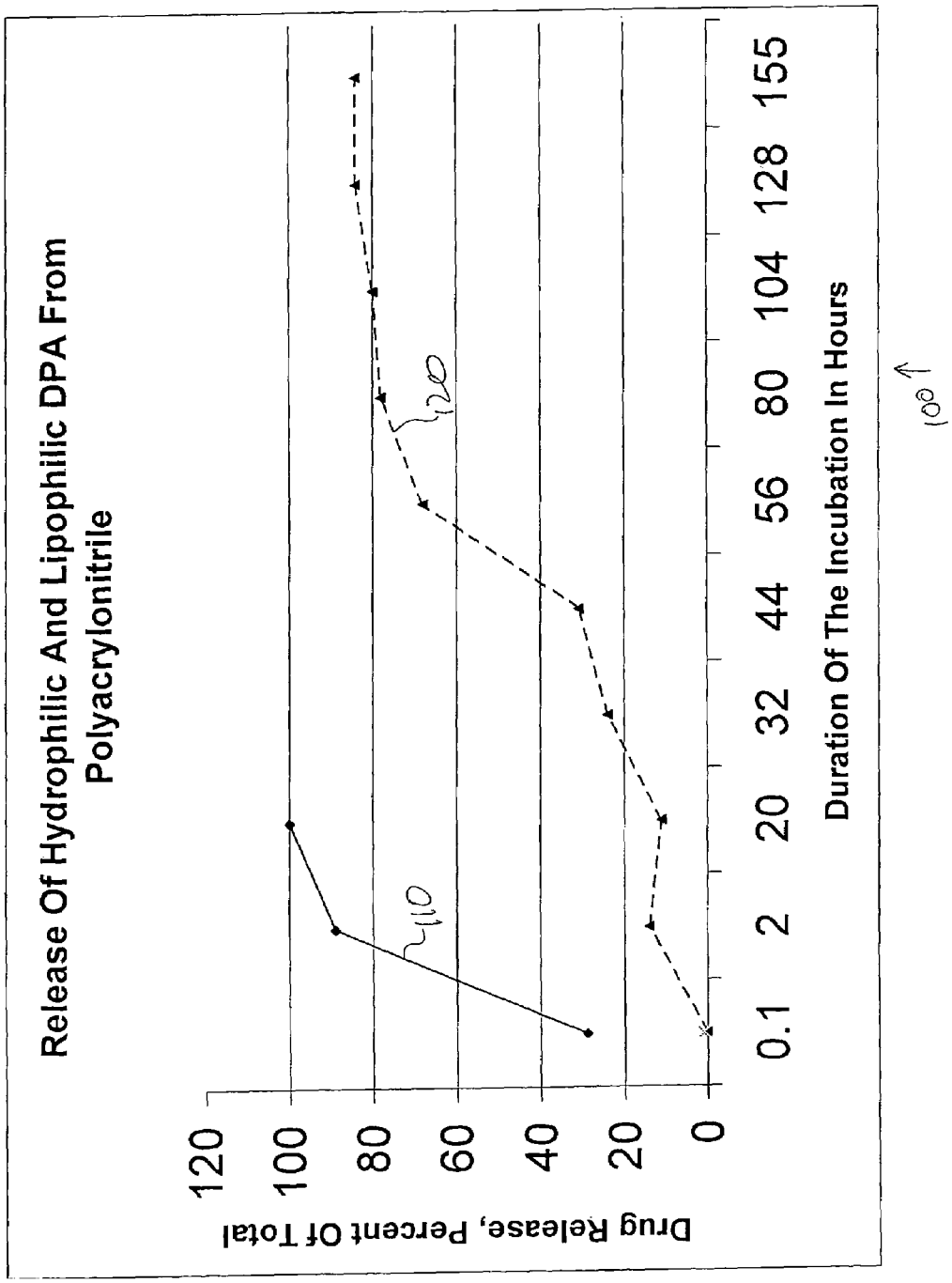
FIG. 1 is a graph showing the release over time of hydrophilic DPA and a lipophilic derivative of DPA from a polymeric carrier.

This invention is described in preferred embodiments in the following description. The preferred embodiments are described with reference to the Figures. The invention will be described as embodied in one of more lipophilic lathyrogenic materials comprising one or more of Compound I, Compound II, Compound III, Compound IV, Compound V, and mixtures thereof.

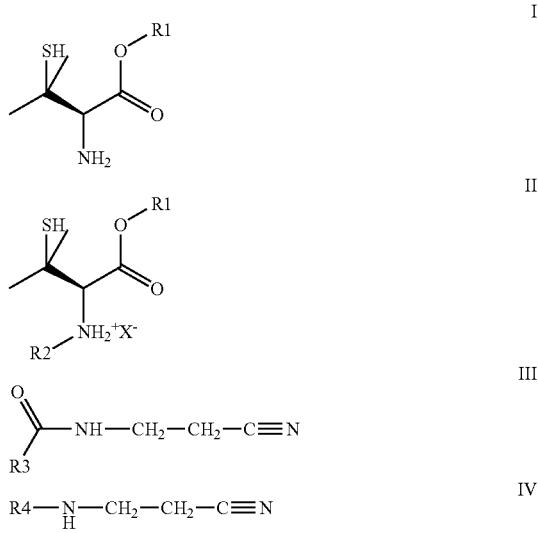

-continued

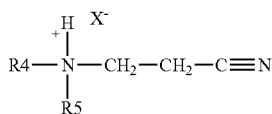

wherein R1 is selected from the group consisting of alkyl, cycloalkyl, phenyl, and benzyl, and wherein R2 is selected from the group consisting of hydrogen, alkyl, cycloalkyl, phenyl, and benzyl, and wherein R3 is selected from the group consisting of alkyl, cycloalkyl, phenyl, and benzyl, and wherein R4 is selected from the group consisting of alkyl, cycloalkyl, phenyl, and benzyl, and wherein R5 is selected from the group consisting of hydrogen, alkyl, cycloalkyl, phenyl, and benzyl, and wherein X⁻ is selected from the group consisting of fluoride, chloride, iodide, acetate, fumarate, propionate, benzoate, and the like, and combinations thereof.

The following description of Applicant's composition and method to inhibit the growth of solid tumors in animals, including humans, is not meant, however, to limit Applicant's invention to use of DPA, and/or derivatives of DPA, and/or BAPN, and/or derivatives of BAPN, as the invention herein can be applied to inhibiting the growth of solid tumors using one or more lipophilic lathyrogenic derivatives.

By "lathyrogen," Applicant means a substance or combination of substances that produces lathyrism. As those skilled in the art will appreciate, a lathyrogen interferes with the covalent crosslinks in collagen structure which results in the weakening of the mechanical strength of collagen rich tissues. Thus, it leads to bone deformities-osteoporosis, vessel aneurysms, thinning of the skin. The name comes from *lathyrus odoratus*, sweet pea, containing the effective substance BAPN which was consumed by some cultures and produced the above pathologies.

By "lipophilic," Applicant means a material having an octanol/water Partition Coefficient (oil/water) greater than about 1. By "hydrophilic," Applicant means a material having an octanol/water Partition Coefficient less than about 1. As those skilled in the art will appreciate, a Partition Coefficient (oil/water) is a measure of a drug's lipophilicity. That Partition Coefficient is defined as the ratio of un-ionized drug distributed between the organic and aqueous phases at equilibrium.

$$P_{o/w} = (C_{oil}/C_{water})_{eqilibrium}$$

The Partition Coefficient is commonly determined using an oil phase of octanol, or chloroform, and water.

For drug delivery, the lipophilic/hydrophilic balance has been shown to be a contributing factor for the rate and extent of drug absorption. Since biological membranes are lipoidal in nature, the rate of drug transfer for passively absorbed drugs is directly related to the lipophilicity of the molecule. Therefore, derivatizing a lathyrogen to increase the Partition Coefficient decreases the rate at which tissue fluids will "wash out" the lipophilic lathyrogen from an injection site, and increases the rate of transfer of that lipohilic lathyrogen through biological membranes.

Mechanisms of action for DPA and BAPN to inhibit tumor growth are summarized in Scheme I.

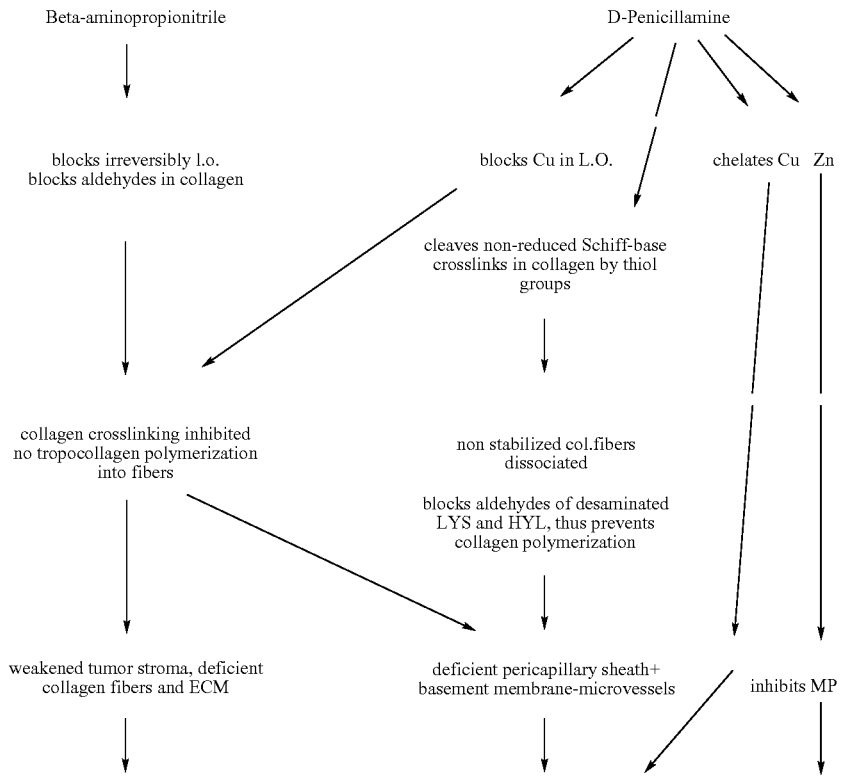

SCHEME I

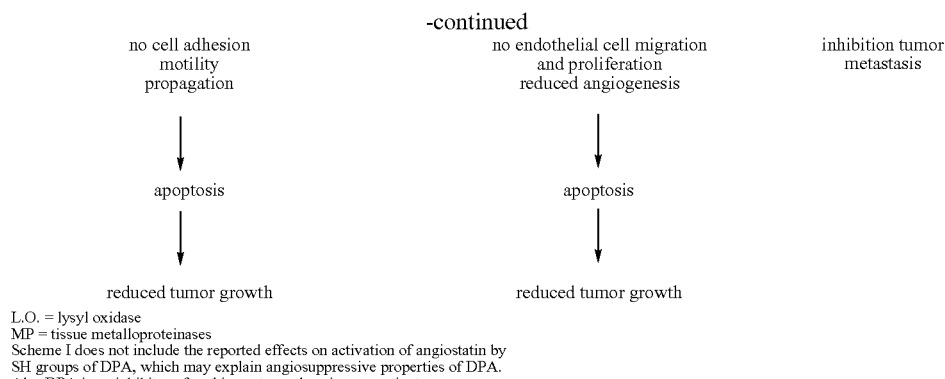

| no cell adhesion<br>motility<br>propagation | no endothelial cell migration<br>and proliferation<br>reduced angiogenesis | inhibition tumor<br>metastasis |

↓ ↓ apoptosis    apoptosis

↓ ↓ reduced tumor growth    reduced tumor growth

L.O. = lysyl oxidase
MP = tissue metalloproteinases
Scheme I does not include the reported effects on activation of angiostatin by
SH groups of DPA, which may explain angiosuppressive properties of DPA.
Also DPA is an inhibitor of urokinase-type plasminogen activator In short summary, copper comprises a co-factor for the enzyme lysyl oxidase. DPA complexes with the copper co-factor and thereby inhibits the first step in the crosslinking of collagen. As a consequence DPA blocks formation of collagen fibers and related structures (tumor stroma, pericapillary sheath, basement membrane of microvessels). Furthermore, the S-H moiety cleaves non-reduced Schiff base crosslinks in collagen, thereby dissociating already formed, but not stabilized, collagen fibers.

Still further, DPA blocks already existing aldehydes, formed by oxidative desamination of LYS and HYL residues in collagen by the effect of lysyl oxidase. By this mechanism DPA also prevents polymerization of collagen molecules into fiber form. These three effects result in disintegration of Extra Cellular Matrix ("ECM"), thereby weakening collagen stroma. By inhibiting support for cell adhesion, DPA inhibits tumor cells mobility and propagation. DPA also stops angiogenesis due to faulty ECM.

DPA also chelates copper in the tumor tissue. Copper is considered an obligatory factor in angiogenesis. Therefore, by complexing with copper in the tumor tissue, DPA interferes with angiogenesis. DPA also chelates zinc, which is an essential cofactor in many of the identified tumor metalloproteinases. These enzymes are responsible for tumor metastases.

Still further, DPA, through its S-H group, generates angiostatin (Gately et al 1997), which may explain another aspect of angiosuppressive properties of penicillamine. Angiostatin is an endogenous inhibitor of angiogenesis and tumor growth, inducing apoptosis of endothelial cells.

Still further, DPA inhibits urokinase-type plasminogen activator, which is responsible for endothelial and tumor cells invasion. As an antioxidant, DPA decreases the concentration of free radicals, due to the presence of SH group. In addition, DPA forms hydrogen peroxide in the presence of copper ions thus inhibiting endothelial cells proliferation.

Applicant's method derivatizes a water-soluble lathyrogen, i.e. a hydrophilic lathyrogen, to form a water-insoluble compound, i.e. a lipophilic lathyrogen. Injecting one or more of such lipophilic lathyrogens into a tumor gives a sustained release of the lipophilic lathyrogen over a period of weeks. Incorporating the modified lathyrogen into a biodegradable, natural or synthetic, polymeric carrier further decreases the rate of release of the modified drug complex into tissues. In certain embodiments, Applicant's method includes disposing one or more lipophilic lathyrogenic derivatives into one or more polymeric carriers, and disposing that polymeric carrier/derivatized lathyrogen formulation into a tumor.

By "polymeric carrier," Applicant means a pharmaceutically acceptable material having a number average molecular weight greater than about 500 Daltons, where that material is suitable for use in contact with the tissues of humans and lower animals without undue toxicity, incompatibility, instability, irritation, and the like, commensurate with a reasonable benefit/risk ratio.

In certain embodiments, the one or more polymeric carriers are both pharmaceutically acceptable and biodegradable. In certain embodiments, these one or more biocompatible/biodegradable polymeric systems include sodium hyaluronate, reconstituted fibrin-thrombin system, sodium alginate, chitosan, polyvinylalcohol, polyvinylpyrrolidone, CMC, dextran, polyacrylic acid, polylactate, polyglycolate, and mixtures thereof. The high viscosity, tissue adhesiveness, or gelling, of these polymers provide additional mechanisms to further reduce the rate of release of one or more derivatized lathyrogens from that polymeric carrier.

Applicant has discovered that incorporating a modified lathyrogen into a polymeric carrier, and disposing that polymeric carrier/modified lathyrogen combination one time into a tumor inhibits the growth of that tumor, and promotes regression of that tumor.

Applicant chemically modified two hydrophilic lathyrogens, i.e. DPA and BAPN, both freely soluble in aqueous media, to form lipophilic lathyrogens to reduce the "washout" rate from locally injected tissue. The important functional groups in either lathyrogen were not affected by the chemical modification.

In certain embodiments, Applicant's lipophilic lathyrogens are dispersed to form a fine emulsion in a polymeric carrier. In certain embodiments, the polymeric carrier comprises a biocompatible material. In principle, any type of biocompatible polymer can be used as the polymeric carrier. In certain embodiments, Applicant's tumor-growth inhibiting formulation comprises a natural-occurring polymeric carrier including collagen, chitin, polyaspartic acid, fibrinogen-thrombin composition, and mixtures thereof. In certain embodiments, Applicant's polymeric carrier comprises a synthetic, water-insoluble material. Such water-insoluble polymeric carriers may be used because the quantity of residual polymer left in the regressed tumor is negligible.

Application's methods effectively treats solid tumors occuring in animals, including humans. After injecting Applicant's lipophilic lathyrogen, with or without a polymeric carrier, at an established effective dose, into the solid tumor, the tumor stopped growing within few days, and continued to regress to a scab appearance structure, with pronounced cell apoptosis and collapse of the tumor matrix.

The optimal dose of the injected lipophilic lathyrogen depends on the volume of the tumor, and the rate of tumor growth, but not the body weight of the treated subject. Directly injecting the tumor with that optimal effective local dosage of the drug did not produce systemic toxic effects. In the animal models of melanoma or mammary adenocarcinoma no metastasis were observed.

Prior art chemotherapy, immunosuppression therapy, anti-angiogenesis drugs, and other procedures, target molecular and cellular specific features of the tumor cells. These prior art methods have several rather serious toxic side effects, including anemia, hair loss, immune suppression, gastrointestinal problems, and the like.

In marked contrast, Applicant's composition and method targets a tumor tissue component, namely collagen, which provides the stroma, network for tumor cells adhesion, locomotion, and proliferation. The stroma also provides strength to the microvessels to sustain the blood pressure in these arteriols and capillaries. Disintegration of collagen by the locally injected lathyrogenic drugs has no side toxic effects, as those therapeutics are administered at very low dose in comparison with their prior art systemic administration.

The following examples are presented to further illustrate to persons skilled in the art how to make and use Application's invention, and to indentify presently preferred embodiments thereof. These examples are not intended as limitations, however, upon the scope of the invention, which is defined only by the appended claims.

As shown in Scheme II, in certain embodiments Applicant's method to prepare their composition includes reacting DPA with an alcohol R1-OH and/or an alkyl halide R1-Y, wherein Y is selected from the group consisting of fluorine, chlorine, bromine, and iodine, using synthetic methods known in the art, to form ester 1, wherein R1 is selected from the group consisting of methyl, ethyl, propyl, butyl, pentyl, hexyl, phenyl, benzyl, and mixtures thereof.

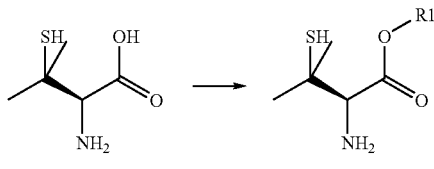

Scheme II

DPA → I

EXAMPLE 1

Synthesis of DPA-Methylester Hydrochloride

In a ice cooled 250 round bottle, 100 ml MeOH and 5 g DPA powder were combined, and 25 ml of thionyl chloride were slowly added by pipet. The reaction mixture was allowed to react for 4 days. No cooling or stirring was necessary. Every second day 5 ml thionyl chloride were added. At the end of the 4$^{th}$ day, the reaction mixture was refluxed for about 2–3-hours. During the refluxing all soluble gas is removed. Under vacuum, the reaction mixture was concentrated to between about 25 to about 50 ml. The released toxic vapors were bubbled through a trap cooled using dry ice in MeOH. The resulting concentrate was precipitated with ether. The yield was almost 75%. The final product was recrystallized using MeOH/ether.

EXAMPLE II

Synthesis of D-Penicillamine Hexylester Hydrochloride

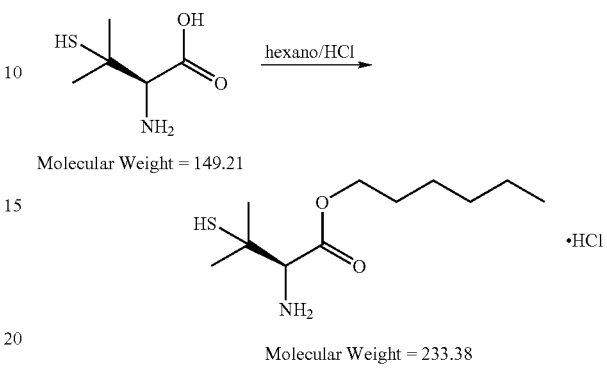

A suspension of DPA (1.64 g, 11.0 mmol) in hexanol was saturated with HCl (50 mL), and then heated at 100° C. for 48 hours. The reaction course was followed using TLC (silica gel plates, development with ethyl acetate-butanol-acetic acid-water (2:1:1:1), detection by spraying with a dilute ethanolic ninhydrin solution). The alcohol was removed in vacuum, the residue was co-distillated with benzene and fresh portion of hexanol saturated with HCl (50 mL) was added. After heating at 100° C. for another 48 hours, the alcohol was removed in vacuum, the residue was dissolved in ethyl acetate, and the organic layer was washed with saturated aqueous NaHCO$_3$ (3×) and water (5×). The product was extracted with 4M HCl (5×), the organic layer was discarded, and the aqueous phase was neutralized with NaHCO$_3$, and then extracted with ethyl acetate (5×). The pooled extracts were washed with water (3×), dried (Na$_2$SO$_4$), solvent was removed in vacuum, and the residue was triturated with petroleum ether to give waxy off-white solid.

Recrystallization from petroleum ether afforded waxy off-white hydrochloride of the title compound. The yield was about 650 mg (24%), mp 92–102° C., R$_f$ 0.8, MW confirmed using MS (both ESI+ and APCI+ modes).

EXAMPLE III

Rate of Release from Polymeric Carrier of Hydrophilic Lathyrogen Compared to Lipophilic Lathyrogen In order to achieve sustained release of a locally injected lathyrogen into tumor tissue, the water solubility of that lathyrogen must be diminished, i.e. the lathyrogen must be converted from a hydrophilic material to a lipophilic material thereby reducing the rate of wash-out from the tissue deposit by tissue fluids.

Applicant compared the rate of release from a polymeric carrier of unmodified DPA, i.e. a hydrophilic lathyrogen, and a lipophilic D-penicillamine adduct formed by reacting DPA with hexanaldehyde using a published synthetic procedure. Both lathyrogens were dispersed in a polyacrylonitrile ("PAN") polymer sold in commerce by SKY Polymers, Princeton, N.J. under the tradename HYPA(N-30). The HYPA(N-30) was dissolved in 100% DMSO.

Water drowning this DMSO/HYPA(N-30)/lipophilic DPA solution, using a syringe with a 16 gauge needle attached, into saline (0.9% NaCl in water W/v) forms a flexible, solid string. The DMSO solution was kept at 37° C., and the incubation jar was minimally shaken. At the times recited in Table 1, an aliquot of the incubation medium was collected and the amount of released D-penicillamine was determined using a reaction between ninhydrin and the free amino groups on the released DPA. In the lipophilic DPA-adduct, the amino groups were originally blocked by the reaction with hexanal, but this linkage is cleaved at temperatures above 45° C. The ninhydrin reaction requires heating the sample at 100° C., thus freeing the amino group. Table 1 recites the results.

TABLE 1

| Time, Hours | Percent of Lipophilic DPA Released | Percent of Hydrophilic DPA Released |
|---|---|---|
| 0.1 | 0 | 29 |
| 2 | 14 | 89 |
| 20 | 11 | 100 |
| 32 | 24 | |
| 44 | 31 | |
| 56 | 68 | |
| 80 | 78 | |
| 104 | 80 | |
| 128 | 84 | |
| 155 | 84 | |

Referring now to FIG. 1, graph 100 depicts the data of Table 1. Curve 110 shows the rate of release of unmodified DPA, i.e. the hydrophilic lathyrogen, from the polymeric carrier as a function of time. Curve 120 shows the rate of release of the modified DPA, i.e., the lipophilic lathyrogen, as a function of time.

Curve 110 shows that the free DPA is quickly released from the polymeric carrier over a few hours. In marked contrast, however, curve 120 shows that after 155 hours only about 80% of the lipophilic DPA adduct was released from the polymeric carrier. The lipophilic DPA adduct was released from the polymer over at least 200 hours.

EXAMPLE IV

Repeated Injections of DPA into Melanoma Tumor

Female mice, standard inbred C 57/Black, having between about 20 to about 25 g body weight were injected s.c. in the right flank region with 0.1 ml of 106 millions B-16 melanoma cells. These cells are harvested in their end of the log phase growth. These cells come from a tissue culture, using RPMI 1640 medium with 10% FBS enriched with 1-glutamine, penicillin and streptomycin. Cells are harvested by trypsinization, counted, suspended in sterile PBS, and injected in 0.1 ml s.c. in flank region. There were 4 mice per group.

Injection of these melanoma cells resulted within 10 days post injection to a tumor weight of about 1.5 g. Tumor volumes were monitored 3× per week by caliper (MITUYO digital, Smalls Parts Inc., Phoenix, Ariz.) in two perpendicular directions and once per week for body weight. Tumor volume in cubic millimeters is calculated by the formula: (length×(width$^2$))/2.

Monitoring was continued up to 4 weeks. When the control animals began to die from the tumor burden, the experiment was terminated. Individual animals were terminated once the tumor volume exceeded 20% of mice weight, or when the body weight loss exceeded 20% of the starting body weight.

Table 2 recites the volume, in cubic millimeters, of the melanoma tumor injected daily with 5 mg DPA in 0.2 ml of saline. The treatment was administered once the tumor reached a detectable and measurable size. The determination of the tumor volume was done at times shown in Table 2. Average volumes are recited in Table 2. After only two injections, tumor volumes in the control group and in the treatment group differed significantly. There was no effect on body weight or animals behavior.

TABLE 2

| | Volumes Of Melanoma Tumor In Non Treated Mice Or In DPA Daily Injected Mice | | | | |
|---|---|---|---|---|---|
| | Days After The Detectable Tumor Was Injected | | | | |
| | 0 | 2 | 5 | 7 | 9 |
| Control | 119 | 800 | 1105 | 3271 | 4958 |
| DPA | 89 | 174* | 806* | 816* | 486* |

(An asterisk indicates a statistically significant difference)

The data of Table 2 illustrate the effectiveness of daily treatment of the tumors by local injection with DPA.

EXAMPLE V

Single Injection of Lipophilic Lathyrogen/Polymeric Carrier into Mammary Carcinoma In this Example V, Applicant prepared a formulation comprising methylester-DPA.HCl, i.e. Compound II wherein R1 is methyl and wherein R2 is hydrogen, and wherein X is chloride, or Hexyl(amino)-propionitrile, i.e. Compound IV, wherein R4 is hexyl, dispersed in a liquid polymeric carrier.

Applicant dispersed 1 gram of either methylester-DPA.HCl, or hexyl(amino) propionitrile, in combination with about 100 mg of the unmodified DPA or BAPN, respectively, in about 1 ml of the liquid polymer. After thorough mixing, 1 ml volume syringes were filled with Applicant's formulation. All preparations were performed at about 4° C., over crushed ice, and the syringes and needles used were refrigerated prior to loading. The loaded syringes were kept in a refrigerated vessel until used.

The rat model of solid tumor was described by Miller et al. (Proc Nat'l Acad Sci 90,3304,1993). Fischer 344 (F344) inbred female rats were used. The initial body weight was 100 grams, plus or minus about 7 grams. The right flank area was clipped, and the rats were tattooed for identification in the ear. A cell line of malignant mammary adenocarcinoma, code 13762 NM, 1 to 10 million viable cells/0.1 ml of MEM was injected s.c. in the right flank through a 24 gauge needle under aseptic conditions. No anesthesia was needed.

After 2 weeks the tumors reached 2,000 μl volume. The animals were killed, and the tumor dissected in a Petri disk with a 1 mm square matrix to allow cutting the tumor tissue into 1 cm cubicles, i.e. chunks. These tumor chunks were dispersed in sterile saline. One tumor chunk was injected into the flank region of each of the rats. The remaining chunks of the tumor were frozen and preserved in liquid nitrogen for use in Example VI.

There were 6 rats per group. The control group had the tumor infiltrated with 0.2 ml of the polymeric carrier. The experimental groups were injected with either Methylester-DPA.HCl or Hexylamino-propionitrile dispersed in 0.2 ml of the polymeric carrier. Once the implanted tumor was detectable, the size of that tumor was measured by caliper in two perpendicular directions.

The growth of each tumor was determined every second day. When the tumor reached 3000 mm$^3$, the animals were terminated by barbital overdose. The tumors were dissected and fixed for morphological analysis, or kept frozen for later biochemical analysis.

At nine days after inoculation, the tumor was detectable. The rats were stratified randomly into 3 groups, each with 6 rats, including: (1) a control group, (2) a group treated on day 10 with a single injection into the tumor with methylester-DPA.HCl in a polymeric carrier, and (3) a group treated on day 10 with a single injection into the tumor with Hexylamino-propionitrile in a polymeric carrier.

Figure 2:
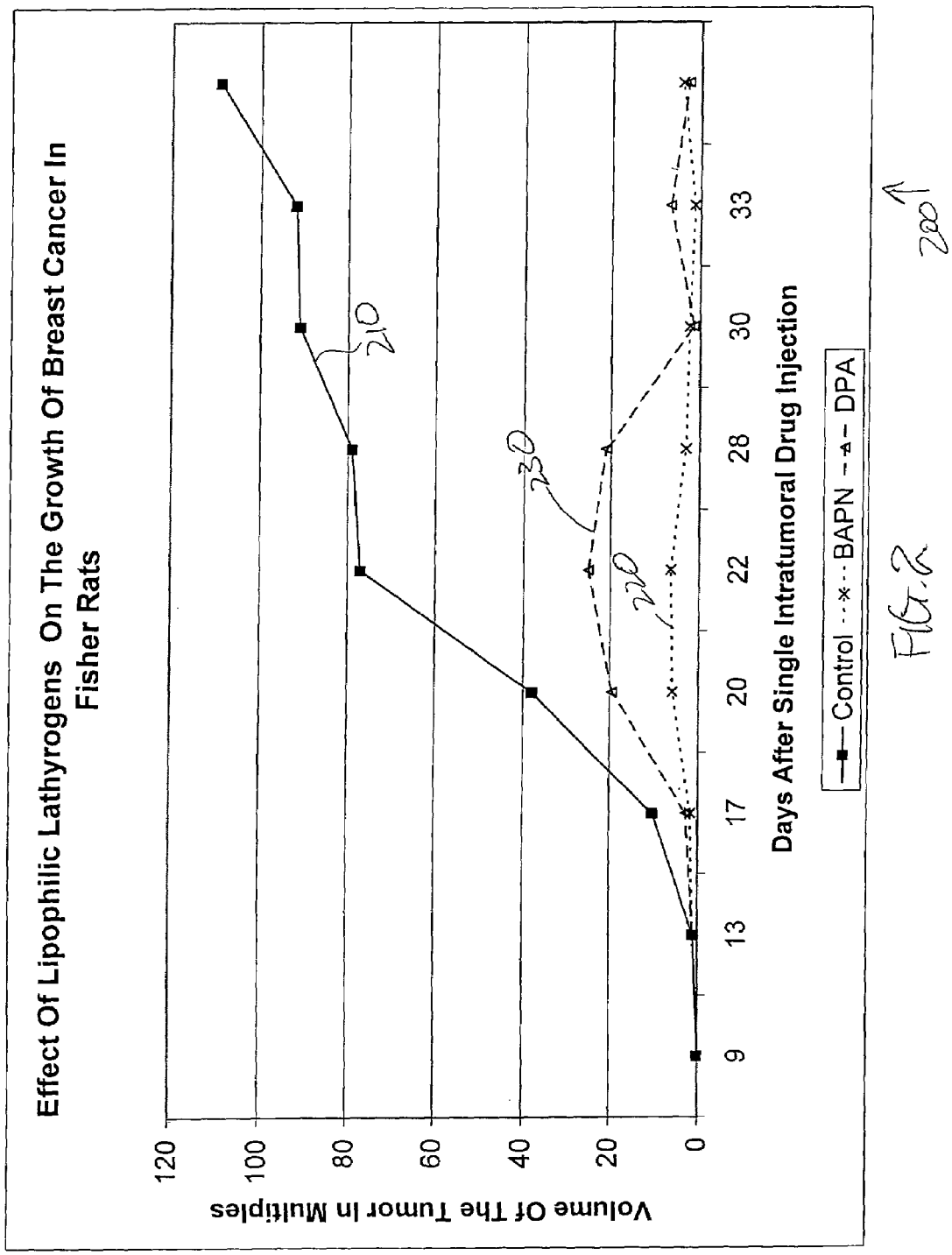
FIG. 2 is a graph showing the effect of a single intratumoral injection of derivatized DPA and BAPN on the growth of mammary carcinoma.

The tumor growth was observed for 33 days. During this time all groups of rats gained the same body weight. FIG. 2 graphically depicts the volume of tumor as a function of time for the control group and the two experimental groups. Referring now to FIG. 2, curve 210 shows the volume of tumor as a function of time for control group 1, i.e. a single injection of the polymeric carrier into the tumor on day 10. Curve 220 shows the volume of tumor as a function of time for the experimental group 2 receiving a single injection of methylester-DPA.HCl/polymeric carrier into the tumor on day 10. Curve 230 shows the volume of tumor as a function of time for the experimental group 3 receiving a single injection of Hexylamino-propionitrile/polymeric carrier into the tumor on day 10.

The curves of tumor growth and its regression for the two experimental groups, i.e. groups 2 and 3 described above, are similar. There is an initial and immediate inhibition of the growth, reflecting the effect of readily available free drugs in the injection material. It is known in the art that free BAPN is active no more than 24 hours, being quickly excreted and metabolized.

Continued inhibition of the tumor growth in groups 2 and 3 is caused by the sustained release of Applicant's lipophilic lathyrogenic compound from its polymeric carrier, where that released lipophilic lathyrogen continuously disrupts collagen structure and metabolism. The second phase of the inhibition and actual tumor regression appears 10 to 12 days after drug injection. This second phase results from the continuous release of, and the concomitant continuous activity of, Applicant's lipophilic lathyrogenic compounds to disintegrate the collagen component of the tumor.

In group 3, three days after injection of the drug the growth of the tumor was markedly inhibited and in later stages showed a regression of the volume. In this group at time of termination of the animals the tumor appeared macroscopically under dissection as a scab, cornified structure. In group 2, from the four surviving rats two showed even more pronounced inhibition of tumor growth resulting in the same scab appearance.

The data depicted in FIG. 2 indicate that the regression of the tumor started 10 to 12 days after the single injection of Applicant's modified lathyrogen/polymeric carrier formulation, and progressed 22 days after the infiltration of the tumor with either drug. It may be that when the tumor under treatment with Applicant's formulation reaches a certain degree of structural and metabolic collapse, the process continues even without the presence of the drug. Alternatively and/or in addition, Applicant's formulation releases active lathyrogen within the tumor tissue for an extended time period, as is suggested by microscopic analysis.

At the autopsy the rats were inspected for the presence of metastasis in the liver and the lung. No metastases were recorded in either group.

Those tumors with inhibited growth using either lathyrogen, and harvested 23 days after drug injection, were characterized by macroscopic evaluation as scab-like. The histology showed no residual tumor present, infiltration with inflammatory cells, spaces indicating the residual drug, and presence of giant cells and abundance of collagenous structures. There was no evidence of the presence of the polymer.

Control tumors collected 19–22 days after inoculation of the tumor chunks and at the death of the rats showed necrosis in the middle of the tumor and abundance of tumor cells.

Another parameter studied was the survival of the rats as a function of tumor growth. It was found that those rats dying mostly after 19 to 22 days of the experiment exhibited a tumor mass of about 7.59 cm$^3$, while in surviving the entire experiment exhibited a tumor mass of about 1.05 cm$^3$. This was a highly significant difference (T=3.84, P<0.01, degree of freedom 14). All the surviving rats were members of either group 2 or group 3.

EXAMPLE VI

Single Injection of Polymeric Carrier into Mammary Carcinoma

In this Example VI, Applicant studied the effect of various treatments on the tumor growth, survival rate, morphology, and metastases in Fisher rats of breast adenocarcinome model. In Experiment V, Applicant documented the inhibitory effect of methylester-DPA.HCl and Hexylamino-propionitrile on the growth of breast tumor. In Experiment VI, these results of Experiment V were verified, and the effects of the polymeric carrier alone and of a one-time injection of methylester-DPA.HCl in water were studied.

The method of Example V was used to prepare and inject tumor chunks into the test animals. In Example VI, Applicant used 5 groups of animals with 8 rats per group. Table 3 summarizes these 5 groups.

TABLE 3

| Groups: | 1. Control, no treatment |
| | 2. Polymeric Carrier only |
| | 3. Hexyl ester DPA.HCI in water |
| | 4. Hexyl ester of DPA.HCI in Polymeric Carrier |
| | 5. Hexyl (amino)propionitrile in Polymeric Carrier |

The preparation of the treatment modalities was as follows:
Group 1. Control
Group 2. Polymer Carrier only; used 1.5 ml polymer+1 ml water (polymer used: 38% PLGA-c-PEG in saline)
Group 3. 2 grams Polymeric Carrier+1.038 grams Hexyl ester DPA.HCl+200 mg DPA
Group 4. 800 mg Hexyl ester DPA.HCl+200 mg DPA+2 ml water
Group 5. 1.5 grams Polymeric Carrier+1.5 grams Hexyl (amino)propionitrile+200 mg BAPN Once mixed, all materials were kept on ice until injection time. The various formulations were injected into the tumor using a 23 gauge needle. The retains of Groups 2, 3, and 5, remained pourable after 2–3 hours at 82° F.

Table 4 recites the day when the animals died and their average tumor mass at death.

TABLE 4

| Group | Death after injection Rx | Number of deaths | Average tumor mass, mm³ |
|---|---|---|---|
| 1 | 8 days | 1 | 7000 |
|  | 12 days | 3 | 8664 |
| 2 | 7 | 1 | 7141 |
| 3 | 12 | 1 | 6174 |
| 4 | 12 | 3 | 7961 |
| 5 | 13 | 1 | 6050 |
|  | 0 | 1 | 384 |

In this study, the tumors grew much faster than in the study of Example V, reaching the deadly tumor weight in about 7 to about 12 days, while in the previous experiment death occurred after 19 to 22 days. The outlying values from each treatment group were discarded and the averages of each group are recited in Table 4.

Figure 3:
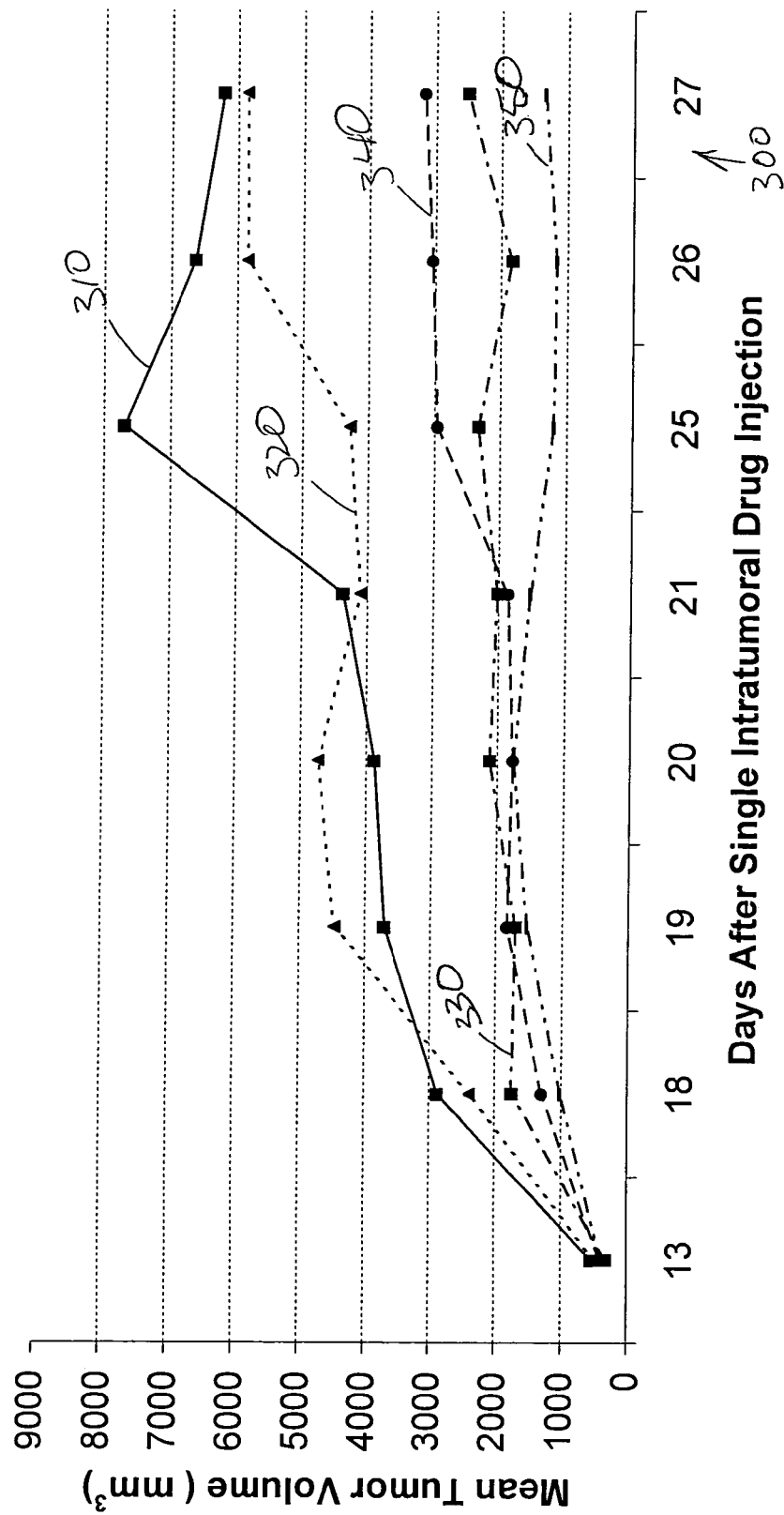
FIG. 3 is a graph showing the effect of a single intratumoral injection of derivatized DPA, dispersed in either water or in a polymeric carrier, and BAPN dispersed in a polymeric carrier, on the growth of breast cancer in Fisher rats.

FIG. 3 graphically depicts the data of Table 4. Referring to FIG. 3, curve 310 shows the rate of tumor growth as a function of time for group 1, i.e. no treatment. Curve 320 shows the rate of tumor growth as a function of time for group 2, i.e. a single injection of the polymeric carrier only. Curves 310 and 320 indicate little difference between the tumor growth of groups 1 and 2.

Curve 330 shows the rate of tumor growth as a function of time for group 3, i.e. a single injection of Methylester-DPA.HCl in the polymeric carrier. Curve 340 shows the rate of tumor growth as a function of time for group 4, i.e. a single injection of Methylester-DPA.HCl in saline. Curve 350 shows the rate of tumor growth as a function of time for group 5, i.e. a single injection of Hexylamino-propionitrile in the polymeric carrier.

Curves 330, 340, and 350, indicate inhibition of tumor growth. No statistical difference was found between these groups. Significantly, a single injection of Methylester-DPA.HCl in saline was effective without the polymer carrier.

While the preferred embodiments of the present invention have been illustrated in detail, it should be apparent that modifications and adaptations to those embodiments may occur to one skilled in the art without departing from the scope of the present invention as set forth in the following claims.

What is claimed is:

1. A method of treating a tumor growing in an animal, including a human, wherein said tumor comprises B-16 melanoma cells or malignant mammary adenocarcinoma, comprising the steps of:
providing a lipophilic lathyrogen;
administering a therapeutically effective amount of said lipophilic lathyrogen within said tumor to a subject in need thereof;
wherein said lipophilic lathyrogen is selected from the group consisting of Compound I, Compound II, Compound III, Compound IV, Compound V, and combinations thereof,

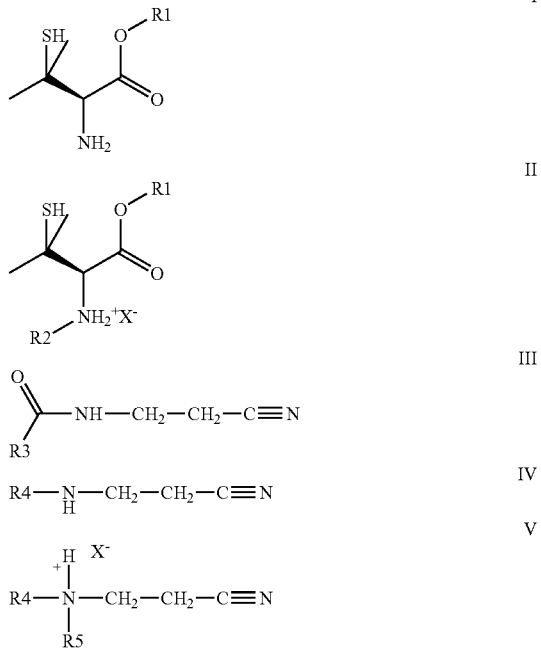

wherein R1 is selected from the group consisting of alkyl, cycloalkyl, phenyl, and benzyl, and wherein R2 is selected from the group consisting of hydrogen, alkyl, cycloalkyl, phenyl, and benzyl, and wherein R3 is selected from the group consisting of alkyl, cycloalkyl, phenyl, and benzyl, and wherein R4 is selected from the group consisting of alkyl, cycloalkyl, phenyl, and benzyl, and wherein R5 is selected from the group consisting of hydrogen, alkyl, cycloalkyl, phenyl, and benzyl, and wherein X⁻ is selected from the group consisting of fluoride, chloride, iodide, acetate, fumarate, propionate, benzoate, and combinations thereof.

2. The method of claim 1, further comprising the steps of:
providiag a polymeric carrier;
dispersing said lipophilic lathyrogen in said polymeric carrier;
disposing said polymeric carrier in said tumor; and
releasing a therapeutically effective amount of said lipophilic lathyrogen from said polymeric carrier over a time period of at least 7 days.

3. The method of claim 2, wherein said polymeric carrier is selected from the group consisting of reconstituted fibrin-thrombin, sodium alginate chitosan, polyvinylalcohol, polyvinylpyrrolidone, CMC, dextran, polyacrylic acid, polylactate, polyglycolate, and mixtures thereof.

4. The method of claim 2, wherein said lipophilic lathyrogen comprises Compound I wherein R1 is methyl.

5. The method of claim 2, wherein said lipophilic lathyrogen comprises Compound I wherein R1 is hexyl.

6. The method of claim 5, further comprising
providing D-Penicillamine;
dispersing said lipophilic lathyrogen and said D-Penicillamine in said polymeric carrier;

administering said polymeric carrier within said tumor; and releasing a therapeutically effective amount of said lipophilic lathyrogen and said D-Penicillamine from said polymeric carrier over a time period of at least 7 days.

7. The method of claim 2, wherein said lipophilic lathyrogen comprises Compound IV wherein R4 is hexyl.

8. The method of claim 7, further comprising the steps of:
providing beta-aminopropionitrile;
dispersing said lipophilic lathyrogen and said beta-aminopropionitrile in said polymeric carrier;
administering said polymeric carrier within said tumor; and releasing a therapeutically effective amount of said lipophilic lathyrogen and said beta-aminopropionitrile from said polymeric carrier over a time period of at least 7 days.

9. The method of claim 2, wherein said lathyrogen comprises Compound I wherein R1 is hexyl, and wherein said polymeric carrier comprises polyacrylonitrile.

* * * * *